(12) United States Patent
Ostrand et al.

(10) Patent No.: US 11,996,121 B2
(45) Date of Patent: May 28, 2024

(54) ACOUSTIC ANALYSIS OF CROWD SOUNDS

(71) Applicant: INTERNATIONAL BUSINESS MACHINES CORPORATION, Armonk, NY (US)

(72) Inventors: Rachel Ostrand, Milford, PA (US); Vagner Figueredo de Santana, São Paulo (BR); Alecio Pedro Delazari Binotto, Munich (DE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 282 days.

(21) Appl. No.: 17/644,363

(22) Filed: Dec. 15, 2021

(65) Prior Publication Data

US 2023/0186942 A1 Jun. 15, 2023

(51) Int. Cl.
*G10L 25/78* (2013.01)
*G06N 20/00* (2019.01)
*G10L 25/21* (2013.01)
*G10L 25/51* (2013.01)
*G10L 25/93* (2013.01)

(52) U.S. Cl.
CPC .............. *G10L 25/78* (2013.01); *G06N 20/00* (2019.01); *G10L 25/21* (2013.01); *G10L 25/51* (2013.01); *G10L 25/93* (2013.01); *G10L 2025/937* (2013.01)

(58) Field of Classification Search
CPC ......... G10L 25/78; G10L 25/51; G10L 25/93; G10L 25/21; G10L 2025/937
See application file for complete search history.

(56) References Cited

U.S. PATENT DOCUMENTS

| | | | |
|---|---|---|---|
| 8,475,396 B2 | 7/2013 | Jones | |
| 10,230,346 B2 | 3/2019 | Jing | |
| 10,773,038 B2 | 9/2020 | Holley | |
| 10,828,009 B2 | 11/2020 | Binotto | |
| 11,504,011 B1* | 11/2022 | Jain | ............ G06N 5/04 |

(Continued)

FOREIGN PATENT DOCUMENTS

| CN | 106214176 B | 12/2016 |
|---|---|---|
| JP | 5191750 B2 | 8/2009 |

OTHER PUBLICATIONS

Ristea, Nicolae-Cătălin, and Radu Tudor Ionescu. "Are you wearing a mask? Improving mask detection from speech using augmentation by cycle-consistent GANs." arXiv preprint arXiv:2006.10147 (2020). (Year: 2020).*

(Continued)

*Primary Examiner* — Anne L Thomas-Homescu
(74) *Attorney, Agent, or Firm* — Rakesh Roy

(57) ABSTRACT

A method, computer system, and a computer program product for detecting face mask usage based on a crowd sound is provided. The present invention may include capturing an audio stream including a crowd voice data. The present invention may also include analyzing the crowd voice data using a machine learning model to determine an amount of people wearing masks. The present invention may further include in response to determining that the amount of people wearing masks does not meet a compliance threshold, displaying a content to promote face mask usage.

20 Claims, 7 Drawing Sheets

(56) References Cited

U.S. PATENT DOCUMENTS

| | | | | |
|---|---|---|---|---|
| 2015/0380013 | A1* | 12/2015 | Nongpiur | G10L 25/51 |
| | | | | 704/231 |
| 2016/0071526 | A1* | 3/2016 | Wingate | G01S 3/807 |
| | | | | 704/233 |
| 2016/0125882 | A1* | 5/2016 | Contolini | H04R 3/005 |
| | | | | 704/231 |
| 2016/0142462 | A1* | 5/2016 | Johnston | G10L 17/00 |
| | | | | 709/205 |
| 2019/0318746 | A1* | 10/2019 | Kano | G06V 20/59 |
| 2021/0280193 | A1* | 9/2021 | Goldstein | G10L 21/028 |
| 2022/0232332 | A1* | 7/2022 | Goff | H04R 3/005 |
| 2023/0005498 | A1* | 1/2023 | Clark | G10L 25/78 |

OTHER PUBLICATIONS

Amin, Prithvi N., et al. "Deep learning based face mask detection and crowd counting." 2021 6th International Conference for Convergence in Technology (I2CT). IEEE, 2021. (Year: 2021).*

Das, et al., "Classification of Speech with and without Face Mask using Acoustic Features", arXiv:2010.03907v1 [eess.AS], Oct. 8, 2020, 6 Pages. https://arxiv.org/pdf/2010.03907.pdf.

Fiorella, et al., "Voice Differences When Wearing and Not Wearing A Surgical Mask", Jan. 26, 2021, vf Journal of Voice, 7 Pages. https://www.jvoice.org/article/S0892-1997(21)00070-9/fulltext.

Llamas, et al. "Effects of Different Types of Face Coverings on Speech Acoustics and Intelligibility", CiteSeer, Retrieved from Internet Dec. 8, 2021, 1 Page. http://citeseerx.ist.psu.edu/viewdoc/summary?doi=10.1.1.483.644.

Magee, "Effects of Face Masks on Acoustic Analysis and Speech Perception: Implications for Peri-Pandemic Protocols", The Journal of the Acoustical Society of America, Nov. 14, 2020, 31 Pages. https://doi.org/10.1121/10.0002873.

Mell et al., "The NIST Definition of Cloud Computing", Recommendations of the National Institute of Standards and Technology, NIST Special Publication 800-145, Sep. 2011, 7 pages.

Nguyen, et al., "Acoustic Voice Characteristics With and Without Wearing a Facemask", Scientific Reports, 2021, 11 Pages. https://www.nature.com/articles/s41598-021-85130-8.

Ristea, et al., "Are you wearing a mask? Improving mask detection from speech using augmentation by cycle-consistent GANs", arXiv:2006.10147v2 [eess.AS], Jul. 25, 2020, 5 Pages. https://arxiv.org/abs/2006.10147v2.

Saeidi, et al., "Analysis of Face Mask Effect on Speaker Recognition", Interspeech, Sep. 8-12, 2016, 6 Pages. https://www.researchgate.net/publication/307889626_Analysis_of_Face_Mask_Effect_on_Speaker_Recognition.

Saeidi, et al., "Speaker Recognition For Speech Under Face Cover", ISCA (the International Speech Communication Association), 2015, 6 pages. https://erepo.uef.fi/bitstream/handle/123456789/4370/saeidi_speaker_2015.pdf?sequence=1&isAllowed=y.

Toscano, et al., "Effects of Masks on Speech Recognition in Multi-Talker Babble Noise", Plos One, Feb. 24, 2021, 12 Pages. https://journals.plos.org/plosone/article?id=10.1371/journal.pone.0246842.

Wu, et al., "Mask Detection and Breath Monitoring From Speech: on Data Augmentation, Feature Representation and Modeling", arXiv:2008.05175v2 [eess.AS], Aug. 14, 2020, 5 Pages. https://arxiv.org/abs/2008.05175v2.

Sensory, "Finally, a Biometric Solution That Recognizes Users Wearing Face Mask and Doesn't Require Touch," Sensory, Jun. 2, 2020, 3 pgs., Retrieved from the Internet:https://www.prnewswire.com/news-releases/finally-a-biometric-solution-that-recognizes-users-wearing-face-masks-and-doesnt-require-touch-301069400.html.

* cited by examiner

ACOUSTIC ANALYSIS OF CROWD SOUNDS

BACKGROUND

The present invention relates generally to the field of computing, and more particularly to acoustics.

Near-universal face mask usage has been identified as an important measure to curb the spread of viruses, such as severe acute respiratory syndrome coronavirus 2 (SARS-CoV-2). As a result, it may be important for companies, health organizations, and/or government authorities to be able to assess what percentage of a population are wearing face masks. In particular, it may be important to understand whether certain geographic areas have poor mask-wearing compliance (e.g., certain neighborhoods of a city; certain types of public transportation; certain office buildings). Existing solutions for determining mask-wearing compliance may raise privacy and logistical concerns.

SUMMARY

Embodiments of the present invention disclose a method, computer system, and a computer program product for detecting face mask usage based on a crowd sound. The present invention may include capturing an audio stream including a crowd voice data. The present invention may also include analyzing the crowd voice data using a machine learning model to determine an amount of people wearing masks. The present invention may further include in response to determining that the amount of people wearing masks does not meet a compliance threshold, displaying a content to promote face mask usage.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
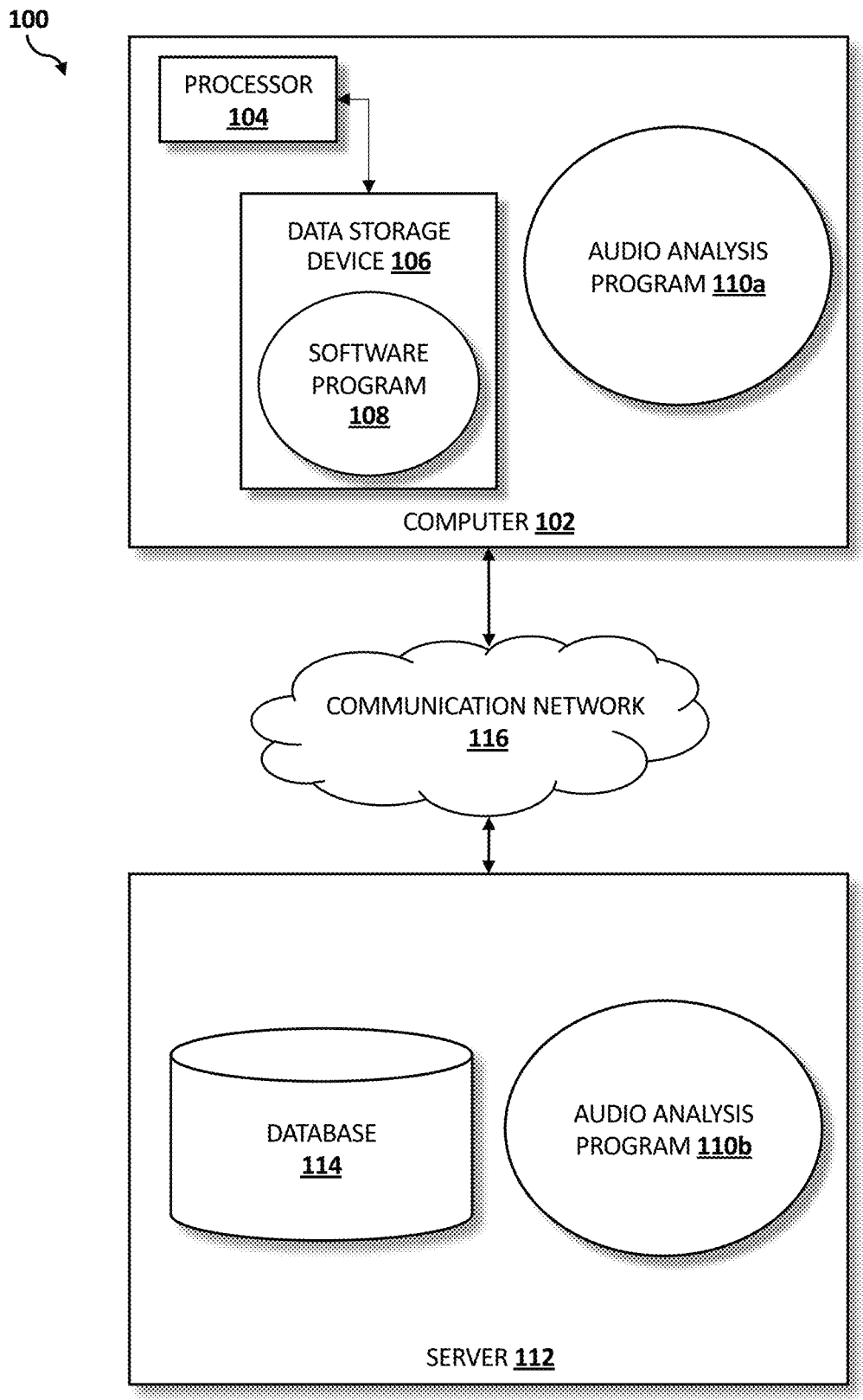
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions collectively stored thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, Python, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for identifying face mask usage in public spaces using acoustic analysis. As such, the present embodiment has the capacity to improve the technical field of acoustics and public health by analyzing acoustic processing of speech to assess mask-wearing compliance. More specifically, an audio analysis program may analyze acoustic data to determine a percentage of mask usage by a group of people in an entirely privacy-preserving way. According to one embodiment, the audio analysis program may receive acoustic data containing human voices from a plurality of people. In one embodiment, the audio analysis program may analyze the acoustic data using a machine learning (ML) model that is trained to determine mask-wearing compliance in a group of people. Thereafter, the audio analysis program may output a percentage of people wearing masks in the plurality of people.

As described previously, near-universal face mask usage has been identified as an important measure to curb the spread of viruses, such as SARS-CoV-2. As a result, it may be important for companies, health organizations, and/or government authorities to be able to assess what percentage of a population are wearing face masks. In particular, it may be important to understand whether certain geographic areas have poor mask-wearing compliance (e.g., certain neighborhoods of a city; certain types of public transportation; certain office buildings). Existing solutions for determining mask-wearing compliance may raise privacy and logistical concerns.

Therefore, it may be advantageous to, among other things, provide a way to determine mask-wearing compliance in a privacy-preserving manner based on measuring raw acoustic properties, such that no semantic or lexical contents are recorded, measured, or analyzed. It may also be advantageous to leverage edge computing by processing acoustic data locally and not recording any audio data or sending audio data to the cloud for processing.

According to at least one embodiment of the present disclosure, an audio analysis program may assess face mask-wearing compliance in a group of people based on acoustic processing of an aggregated signal of voices from the group of people. In one embodiment, the acoustic processing may measure one or more acoustic properties of voices which may be affected by wearing a face mask over one's mouth. In one embodiment, the measured acoustic properties may include frequency attenuation or transmission loss resulting from voices propagating through face masks. In particular, it is contemplated that high frequencies may be distorted from wearing face masks.

According to at least one embodiment of the present disclosure, the audio analysis program may assess face mask-wearing compliance in a group of people in an entirely privacy-preserving manner. More specifically, embodiments of the present disclosure is based on measuring raw acoustic properties (e.g., transmission loss; frequency attenuation; power band of certain frequencies), and as such, no semantic or lexical content is recorded, measured, or analyzed. By processing an aggregate signal of voices and measuring raw acoustic properties, embodiments of the present disclosure may preserve the privacy of the speakers as they cannot be identified. Further, embodiments of the present disclosure may leverage edge computing by processing the audio data using local devices without needing to record and transmit the audio data to a cloud platform for remote processing.

According to at least one embodiment of the present disclosure, an array of microphones may be provided in a location or venue that is indoors or outdoors (e.g., street corner, public transit station, office building, traffic stop). In one embodiment, the audio analysis program may implement the array of microphones to capture and process an audio stream of ambient speech that is produced by passers-by. In one embodiment, the audio analysis program may perform on-line processing of the ambient speech using a fast Fourier transform (FFT) to convert the signal from its original domain (e.g., time domain) to a frequency domain. In one embodiment, the FFT may be used to compute a power-frequency distribution for the ambient speech. In one embodiment, the power in different frequency bands associated with the ambient speech may be compared to the power in different frequency bands associated with reference records of crowd noise with different (known) percentages of mask-wearing compliance. For example, reference records may be created with 0%, 25%, 50%, 75%, and 100% of the people wearing masks.

According to at least one embodiment of the present disclosure, the audio analysis program may implement an on-line comparison of the current crowd noise (e.g., ambient speech) against the reference recordings to estimate the current crowd's degree (e.g., percentage) of mask-wearing compliance.

According to at least one embodiment of the present disclosure, the audio analysis program may implement the audio processing to determine a number of people passing-by within proximity of the array of microphones and the amount of people wearing face masks. In one embodiment, the goal of such audio processing is to perform mask-wearing compliance at scale and in a privacy preserving manner, given that no visual recognition nor content spoken are processed.

According to at least one embodiment of the present disclosure, an array of microphones may be provided in a location or venue that is indoors or outdoors (e.g., street corner, public transit station, office building, traffic stop). In one embodiment, the audio analysis program may implement the array of microphones to capture and process an audio stream of environmental sounds (e.g., ambient speech that is produced by passers-by). In one embodiment, the audio analysis program may separate the captured sounds and identify a source of each separated sound. The separation of the acquired sounds can be performed to, for example, separate sounds of interest (e.g., ambient speech) from background noise, separate two sounds of interest from one-another (e.g., separating multiple speaker sounds), and count the total number of sound sources of interest in the environment. In one embodiment, the audio analysis program may train an ML model to classify a sound source as either wearing a face mask or not wearing a face mask based on acoustic frequency properties discussed further below. In one embodiment, the audio analysis program may then classify each sound source (e.g., individual channel) against the trained ML model. In one embodiment, the audio analysis program may use the output of the trained ML model to count the number of sound sources that may be wearing a face mask and the number of sound sources that may not be wearing a face mask. In one embodiment, the audio analysis program may calculate a percentage of people wearing a face mask in a given environment or venue (e.g., dividing number of sound sources wearing a face mask by total number of sound sources).

Although the present disclosure describes the detection of face masks based on raw acoustic properties, it is contemplated that the audio analysis program may be generalized and implemented in any detection on the frequency domain. For example, the audio analysis program may be implemented to detect "shortness of breath," which may provide an important use case in the field of healthcare. In this example, the audio analysis program may be implemented to identify the frequency range associated with the respiration condition of "shortness of breath" and train an ML model to detect (e.g., classify) that condition. Then, the audio analysis program may be implemented to capture the environmental sounds, as described in the present disclosure, and classify the amount (e.g., percentage) of people with respiration conditions in a crowd in a given environment or venue.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an acoustic analysis program 110a. The networked computer environment 100 may also include a server 112 that is enabled to run an acoustic analysis program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 5, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the acoustic analysis program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the acoustic analysis program 110a, 110b (respectively) to detect face mask usage based on crowd sounds. The disclosed embodiments are explained in more detail below with respect to FIGS. 2 to 4.

Figure 2:
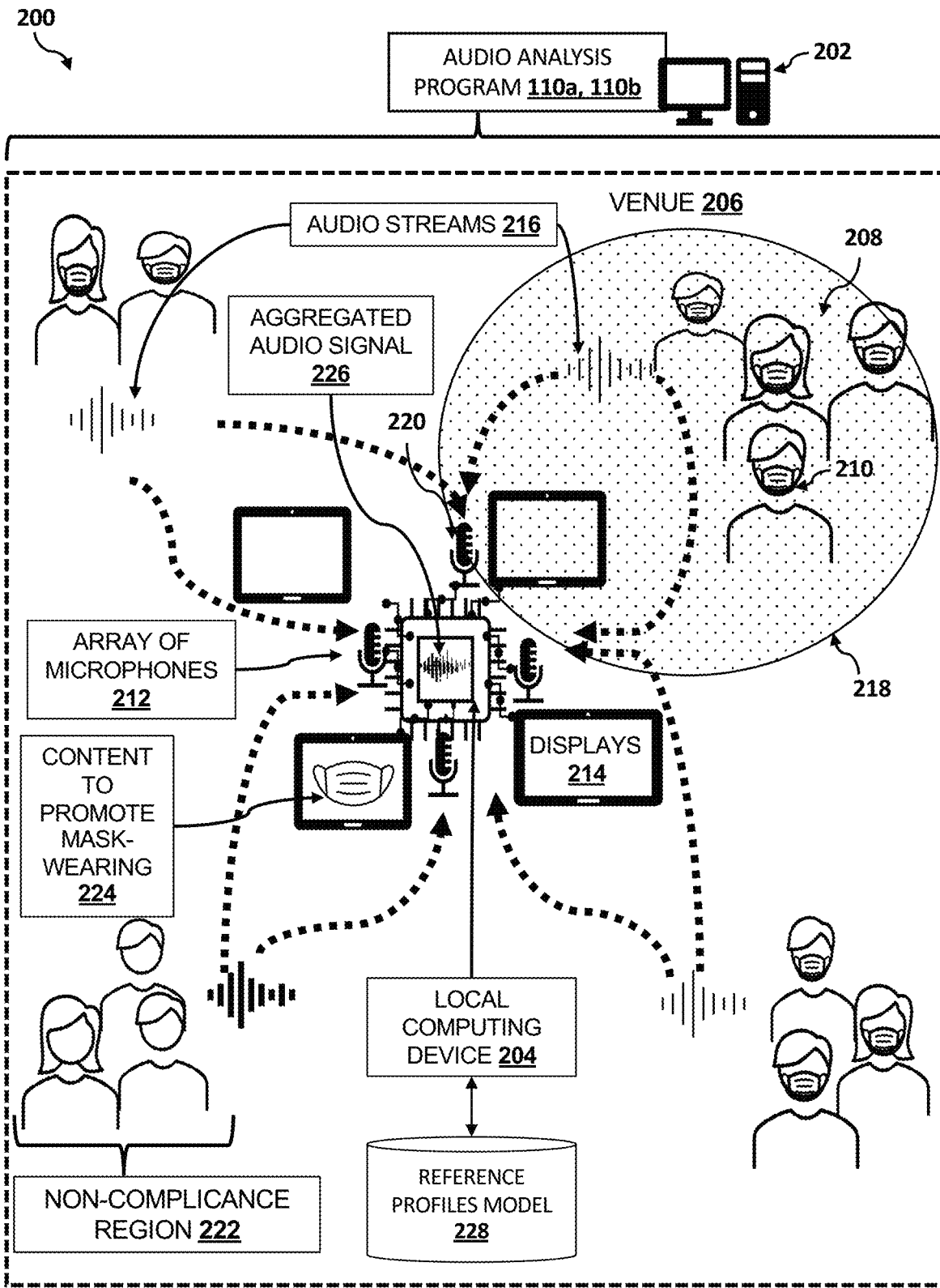
FIG. 2 is a schematic block diagram of an audio analysis environment according to at least one embodiment.

Referring now to FIG. 2, a schematic block diagram of an audio analysis environment 200 implementing the audio analysis program 110a, 110b according to at least one embodiment is depicted. FIG. 2 provides an overview of the audio analysis environment 200, which will be detailed further with reference to FIGS. 3 and 4.

According to one embodiment, the audio analysis environment 200 may include a computer system 202 having a tangible storage device and a processor that is enabled to run the audio analysis program 110a, 110b. In one embodiment, the computer system 202 may include at least one local computing device 204 (e.g., client computer 102) running an instance of the audio analysis program 110a, 110b. In various embodiments, the local device 204 of the computer system 302 may include a workstation, a personal computing device, a laptop computer, a desktop computer, a computing server, a thin-client terminal, a tablet computer, a smartphone, a smart watch or other smart wearable device, or other electronic devices. Although not specifically illustrated in FIG. 2, in some embodiments, the computer system 202 may also include at least one remote computing device (e.g., server computer 112). In at least one embodiment, the remote computing device may also operate in a cloud computing service model, such as Software as a Service (SaaS), Platform as a Service (PaaS), or Infrastructure as a Service (IaaS). In one embodiment, the remote computing device may also be located in a cloud computing deployment model, such as a private cloud, community cloud, public cloud, or hybrid cloud.

According to one embodiment, the audio analysis environment 200 may be deployed in association with a venue 206, which may include, an indoor space, an outdoor space, a hybrid space (e.g., semi-indoor, semi-outdoor), a neighborhood, a city, and/other a geographically bounded region. Examples of venue 206 may include, without limitations, a building, a school campus, a shopping complex, an airport, a train/bus station, a stadium, or any other indoor/outdoor/hybrid environment/geographic region where people may occupy in groups 208 or crowds and move through various locations and perform various activities (e.g., work, commute, shop, study). In some embodiments, one or more people in the groups 208 may wear face masks 210 to comply with public health policies, such as, for example, to disrupt the transmission of a virus. However, in such embodiments, one or more other people in the groups 208 may not wear face masks 210. It is contemplated that the location (e.g., within venue 207) of the people who are not wearing face masks 210 may initially be unknown to venue stakeholders and users of the audio analysis program 110a, 110b. As will be discussed further below, the audio analysis program 110a, 110b may be implemented in venue 206 to detect and locate those people in the groups 208 that are not wearing face masks 210 in a privacy preserving manner.

According to one embodiment, the audio analysis environment 200 may provide one or more sensors in venue 206. In at least one embodiment, the sensors may include an array of microphones 212. In some embodiments, the array of microphones 212 may include any suitable type of microphones configured to convert sound into electrical signals. In various embodiments, the array of microphones 212 may include multiple communicatively linked microphones and/or multiple independent microphones. In at least one embodiment, the array of microphones 212 may include a micro-electro-mechanical systems (MEMS) device having one or more amplifiers.

According to one embodiment, the audio analysis environment 200 may also provide one or more displays 214 located throughout the venue 206. In one embodiment, the array of microphones 212 and displays 214 may be components of an audio/video device. In other embodiments, the array of microphones 212 and displays 214 may be individual devices.

According to at least one embodiment of the present disclosure, the array of microphones 212 may detect and capture one or more audio streams 216 in the venue 206. In one embodiment, the audio streams 216 may include background noise (e.g., traffic noise, dogs barking, music) based on the environment of the venue 206. In various embodiments, the background noise captured with the audio streams 216 may be filtered out using suitable acoustic filtering techniques. In one embodiment, the audio streams 216 may be produced by people (e.g., people of groups 208) that may be speaking as they pass by or are proximate to the array of microphones 212. As such, in various embodiments, the audio streams 216 may include voice data (e.g., human vocalized communication) from the people that may be speaking in proximity of the array of microphones 212. In at least one embodiment, the audio streams 216 including the voice data may be directed at the array of microphones 212. In other embodiments, the audio streams 216 including the voice data may be indirect, ambient speech which may also be captured by the array of microphones 212. In one example, ambient speech may be produced by two or more people having a conversation within proximity of the array of microphones 212.

According to one embodiment, the audio analysis program 110a, 110b may implement the audio streams 216 captured by the array of microphones 212 to perform acoustic source localization. In one embodiment, acoustic source localization may enable the audio analysis program 110a, 110b to separate the captured audio streams 216 to separate sounds of interest from background noise, or to separate two sounds of interest from one-another.

According to at least one embodiment, acoustic source localization may include processing the sound to determine a trajectory of the separated sound and/or determine a location of the source using the array of microphones 212 in a sound source localization process. For example, the audio analysis program 110a, 110b may determine a location of a given speaker relative to a location of one or more microphones of the array of microphones 212.

According to one embodiment, the audio analysis program 110a, 110b may divide the venue 206 into one or more configurable zones or regions 218. In one embodiment, these regions 218 may be implemented to logically and/or physically separate portions of the venue 206. In one embodiment, the audio analysis program 110a, 110b may associate a microphone (e.g., of the array of microphones 212) with the region 218 that is closest to the microphone. For example, the audio analysis program 110a, 110b may associate the region 218 with a microphone 220 that is proximate to the region 218. As such, in response to determining that a sound was received by microphone 220 (e.g., by measuring distance and/or direction using triangulation and/or time difference of arrival (TDOA) techniques), the audio analysis program 110a, 110b may determine that the source of the sound (e.g., one or more speakers) may currently be found in region 218 of the venue 206. According to one embodiment, in addition to determining the location (e.g., region 218) of the speakers in the venue 206, the audio analysis program 110a, 110b may use the acoustic source localization process to determine a total number of people within the venue 206.

According to one embodiment, the audio analysis program 110a, 110b may also associate one or more displays 214 with the region 218 that is closest to the displays 214. As such, in response to the audio analysis program 110a, 110b detecting one or more non-compliance regions 222 (e.g., subset of regions 218) of the venue 206 where one or more speakers may not be wearing face masks 210, the audio analysis program 110a, 110b may present content to promote mask wearing 224 on the display 214 that is proximate to the non-compliance region 222.

According to one embodiment, the audio analysis program 110a, 110b may determine the non-compliance regions 222 based on processing the voice data in the audio streams 216 captured by the array of microphones 212. Although the voice data captured by the array of microphones 212 may be associated with speech, it is contemplated that the audio analysis program 110a, 110b may refrain from processing the voice data for speech recognition purposes in order to safeguard the privacy of the speakers (e.g., no semantic or lexical content is recorded, measured, or analyzed). Instead, the audio analysis program 110a, 110b may process the voice data to measure raw acoustic properties, such as, the pitch (e.g., frequency) and loudness (e.g., intensity; amplitude) of the speakers in the venue 206. More specifically, in various embodiments, the array of microphones 212 may convey the multiple audio streams 216 to the local computing device 204 as an aggregated audio signal 226. In one embodiment, the aggregated audio signal 226 may include an aggregation of voice data associated with a plurality of conversations and speakers. As such, the audio analysis program 110a, 110b may measure the raw acoustic properties based on the aggregated audio signal 226.

According to one embodiment, the aggregated audio signal 226 received by the local computing device 204 may include a time-domain representation. It is contemplated that the time-domain representation of the aggregated audio signal 226 may illustrate how the aggregated audio signal 226 over time. However, in order to determine whether people in the groups 208 are wearing face masks 210, the audio analysis program 110a, 110b may detect sound attenuation resulting from transmission loss. Transmission loss is a noted characteristic of a material (e.g., material of face mask 210) and is frequency dependent. More specifically, the audio analysis program 110a, 110b may detect a greater degree of sound attenuation and transmission loss in higher bands of the frequency spectrum and may detect a lesser degree of sound attenuation and transmission loss in lower bands of the frequency spectrum. As such, the audio analysis program 110a, 110b may convert the aggregated audio signal 226 from its time-domain representation to a frequency-domain representation to determine how the signal's energy or power (e.g., magnitude) is distributed over a range of frequencies.

According to one embodiment, the audio analysis program 110a, 110b may implement a Fourier transform (FT) to decompose the time-domain representation of the aggregated audio signal 226 into its component frequencies. More specifically, the audio analysis program 110a, 110b may implement a Discrete Fourier transform (DFT) type of the FT. In one embodiment, the audio analysis program 110a, 110b may calculate the DFT using the more efficient fast Fourier transform (FFT). In one embodiment, the output of the FFT of the aggregated audio signal 226 may include a cosine graph with power or magnitude value (e.g., amplitude or signal strength) for each frequency band in the frequency-domain representation of the aggregated audio signal 226. In one embodiment, it is contemplated that the frequency-domain representation of human voice frequencies (e.g., as included in the aggregated audio signal 226) may include a frequency range between 80-4000 hertz (Hz). As such, in one exemplary embodiment, the frequency-domain representation may include a power value (e.g., may be zero) for each of those frequency bands.

As described previously, when a person is wearing face mask 210, the audio analysis program 110a, 110b may detect a greater degree of sound attenuation and transmission loss in higher bands of the frequency spectrum. It is contemplated that sound attenuation, also referred to as frequency attenuation, may be detected based on a decrease in the power (e.g., amplitude or signal strength) in a given frequency band. Thus, in at least one embodiment, frequency attenuation resulting from wearing face mask 210 may be detected based on the decrease in power in the higher frequency bands of the frequency spectrum (e.g., above frequencies of 3000 Hz).

According to one embodiment, the acoustic analysis program 110a, 110b may compare the power distribution of the aggregated audio signal 226 (e.g., power in the different frequency bands) to reference recordings of crowd sounds with different (known) percentages of face mask-wearing compliance. More specifically, the acoustic analysis program 110a, 110b may perform an on-line comparison (e.g., real-time) of current crowd sounds (e.g., captured in the aggregated audio signal 226) against one or more reference records to determine (e.g., estimate) the current crowd's degree of mask-wearing compliance.

According to one embodiment, the acoustic analysis program 110a, 110b may train a knowledge base of reference profiles model 228 associated with the reference records of crowd sounds with different (known) percentages of face mask-wearing compliance. According to at least one embodiment, the reference profiles model 228 may include one or more trained machine learning (ML) models that may be stored in a database accessible to the local computing device 204 configured to perform automatic determinations of the current crowd's degree of mask-wearing compliance.

According to at least one embodiment, the reference profiles model 228 may be learned from a set of labeled audio recordings (e.g., labeled with known percentage of face mask-wearing compliance) stored in the knowledge base. Examples of audio recordings may include recordings from an array-based microphone (MEMS) during a training phase. According to one embodiment, the reference profiles model 228 may include meta-data about one or more features corresponding to each of the audio recordings. According to one embodiment, the meta-data may indicate the power distributions in the frequency spectrum associated with each known percentage of face mask-wearing compliance. In at least one embodiment, the power distributions may be described as a ratio between the power in the high frequency bands (e.g., 3000 Hz and above) and the power across all the frequency bands (e.g., 80-4000 Hz) in the frequency spectrum. In one embodiment, the power in the high frequency bands may be measured as the average power available over the given frequency band (e.g., between 3000-4000 Hz). In one embodiment, the power across all the frequency bands may be described as the total average power of all the frequency components of the signal.

According to one embodiment, the acoustic analysis program 110a, 110b may include in the reference profiles model 228, reference recordings of 0%, 25%, 50%, 78%, and 100% of people wearing face masks. In other embodiment, additional reference recordings with various percentages of people wearing face masks may also be included in the reference profiles model 228. In one embodiment, the meta-data associated with each of these reference recordings may indicate the power distribution or ratio between the power in the high frequency bands and the power across all the frequency bands in the given frequency spectrum.

According to one embodiment, the acoustic analysis program 110a, 110b may compute a current power distribution (e.g., ratio of power in frequency bands affected by mask wearing to power in all voice frequency bands) associated with the current crowd sounds (e.g., captured in the aggregated audio signal 226) and compare that current power distribution to each of the power distributions associated with the various reference recordings. In one embodiment, once the acoustic analysis program 110a, 110b matches the current power distribution to one of the power distributions in the reference profiles model 228, the acoustic analysis program 110a, 110b may determine that percentage of the reference recording as the current crowd's degree of mask-wearing compliance. For example, if the current power distribution or ratio matches the power distribution associated with reference recording of 50% of people wearing face masks, the acoustic analysis program 110a, 110b may infer that 50% of the people in the groups 208 are wearing face masks 210.

According to one embodiment, the reference profiles model 228 may implement a classification model and/or a regression model to process the input of the current power distribution and output a category of the percentage of people wearing face masks and/or the percentage of people not wearing face masks in the venue 206 including a confidence level.

According to one embodiment, if the current crowd's degree of mask-wearing compliance does not meet a configurable compliance threshold (e.g., 75% of people wearing face masks), the audio analysis program 110a, 110b may determine the location of the people that are not wearing face masks 210 (e.g., detect the non-compliance region 222 in venue 206) and transmit one or more content to promote mask-wearing 224 on the one or more displays 214 that are proximate to the non-compliance region 222.

Figure 3:
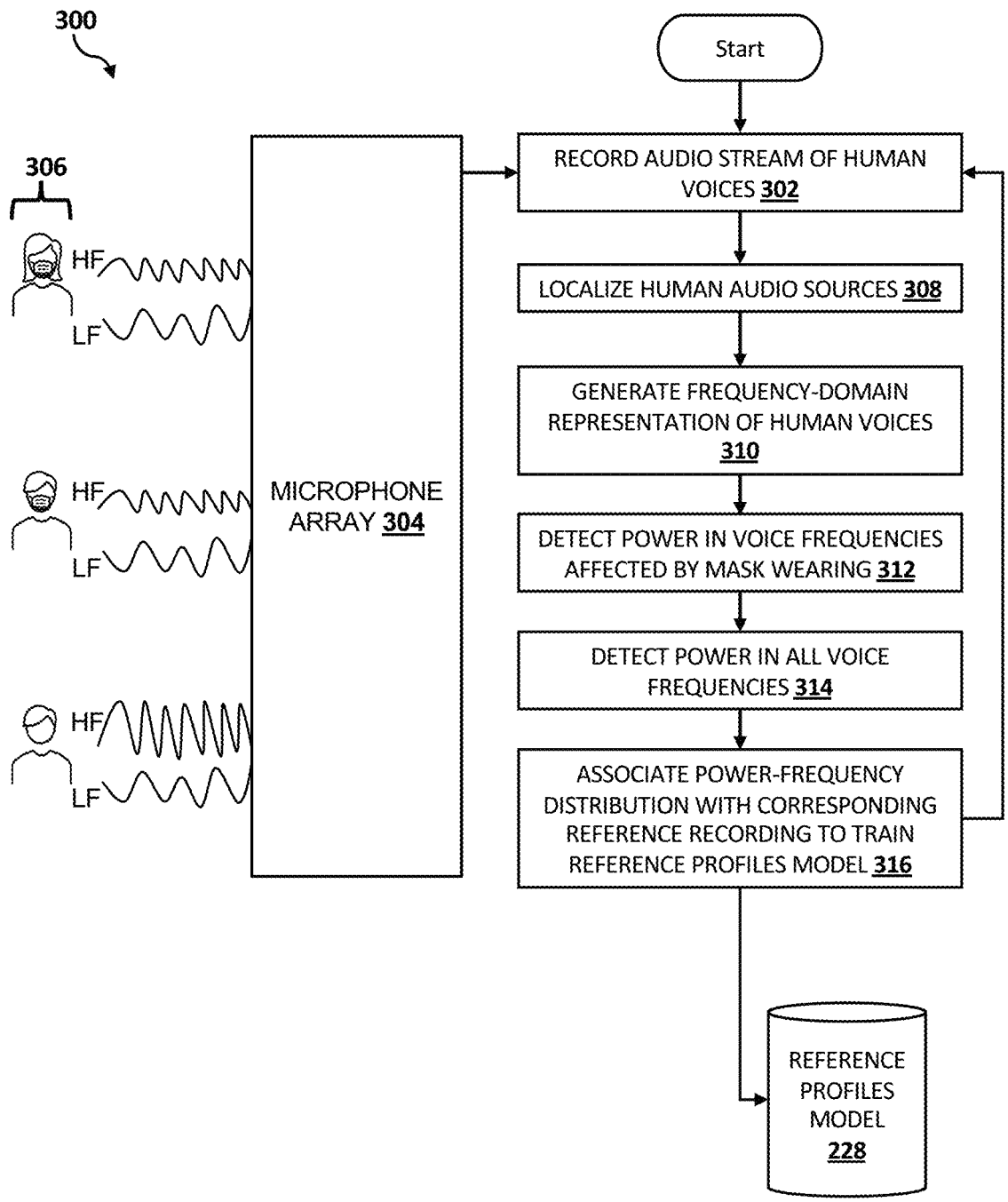
FIG. 3 is an operational flowchart illustrating a process for training machine learning models for acoustic analysis according to at least one embodiment.

Referring to FIG. 3, an operational flowchart illustrating an exemplary training process 300 used by the acoustic analysis program 110a, 110b according to at least one embodiment is depicted.

At 302, an audio stream of human voices are recorded. According to one embodiment, the training process 300 may implement a microphone array 304 (e.g., similar to array of microphones 212 described in FIG. 2) to capture a group of participants 306 speaking, where some of the participants may be wearing a face mask and some of the participants may not be wearing a face mask. According to one embodiment, each of these reference recordings may include meta-data indicating the number of participants 306 and the amount or percentage of the participants that are wearing face masks.

Then at 308, the human audio sources or participants 306 are localized. According to one embodiment, the acoustic analysis program 110a, 110b may detect the distances between each of the participants 306 and the microphone array 304 as described previously with reference to acoustic source localization process in FIG. 2.

Then at 310, a frequency-domain representation of the human voices are generated. According to one embodiment, the recorded audio stream may initially include a time-domain representation. As such, the acoustic analysis program 110a, 110b may convert the time-domain representation of the recorded audio stream using FFT into the frequency-domain representation as described previously with reference to FIG. 2.

Then at 312, the power in voice frequencies affected by mask wearing is detected. As described previously with reference to FIG. 2, when a person is wearing a face mask, the audio analysis program 110a, 110b may detect a greater degree of sound attenuation and transmission loss in higher bands of the frequency spectrum. It is contemplated that sound attenuation, also referred to as frequency attenuation, may be detected based on a decrease in the power (e.g., amplitude or signal strength) in a given frequency band. Thus, in at least one embodiment, frequency attenuation resulting from wearing face mask may be detected based on the decrease in power in the higher frequency bands of the frequency spectrum (e.g., above frequencies of 3000 Hz). In one embodiment, the power in the high frequency bands may be measured as the average power available over the given frequency band (e.g., between 3000-4000 Hz).

Then at 314, the power in all voice frequencies are detected. According to one embodiment, it is contemplated that the frequency-domain representation of human voice frequencies may include a frequency range between 80-4000 Hz. As such, in one exemplary embodiment, the frequency-domain representation may include a power value (e.g., may be zero) for each of those frequency bands. In one embodiment, the power across all the frequency bands may be described as the total average power of all the frequency components of the signal.

Then at 316, a power-frequency distribution is associated with a corresponding reference recording to train the reference profiles model. According to one embodiment, the power-frequency distribution or power distribution may be described as a ratio between the power in the high frequency bands (e.g., 3000 Hz and above) and the power across all the frequency bands (e.g., 80-4000 Hz) in the frequency spectrum. According to one embodiment, the acoustic analysis program 110a, 110b may include in the reference profiles model 228, reference recordings of various percentages (e.g., 0%, 25%, 50%, 78%, and 100%) of people wearing face masks. In one embodiment, the acoustic analysis program 110a, 110b may associate each of these reference recordings with the corresponding power distribution or ratio calculated from process 312 and 314. According to one embodiment, the power distributions may be associated with the corresponding reference recordings as meta-data. In one embodiment, the acoustic analysis program 110a, 110b may train the reference profiles model 228 as a classification model. In other embodiments, the acoustic analysis program 110a, 110b may train the reference profiles model 228 as a regression model.

Figure 4:
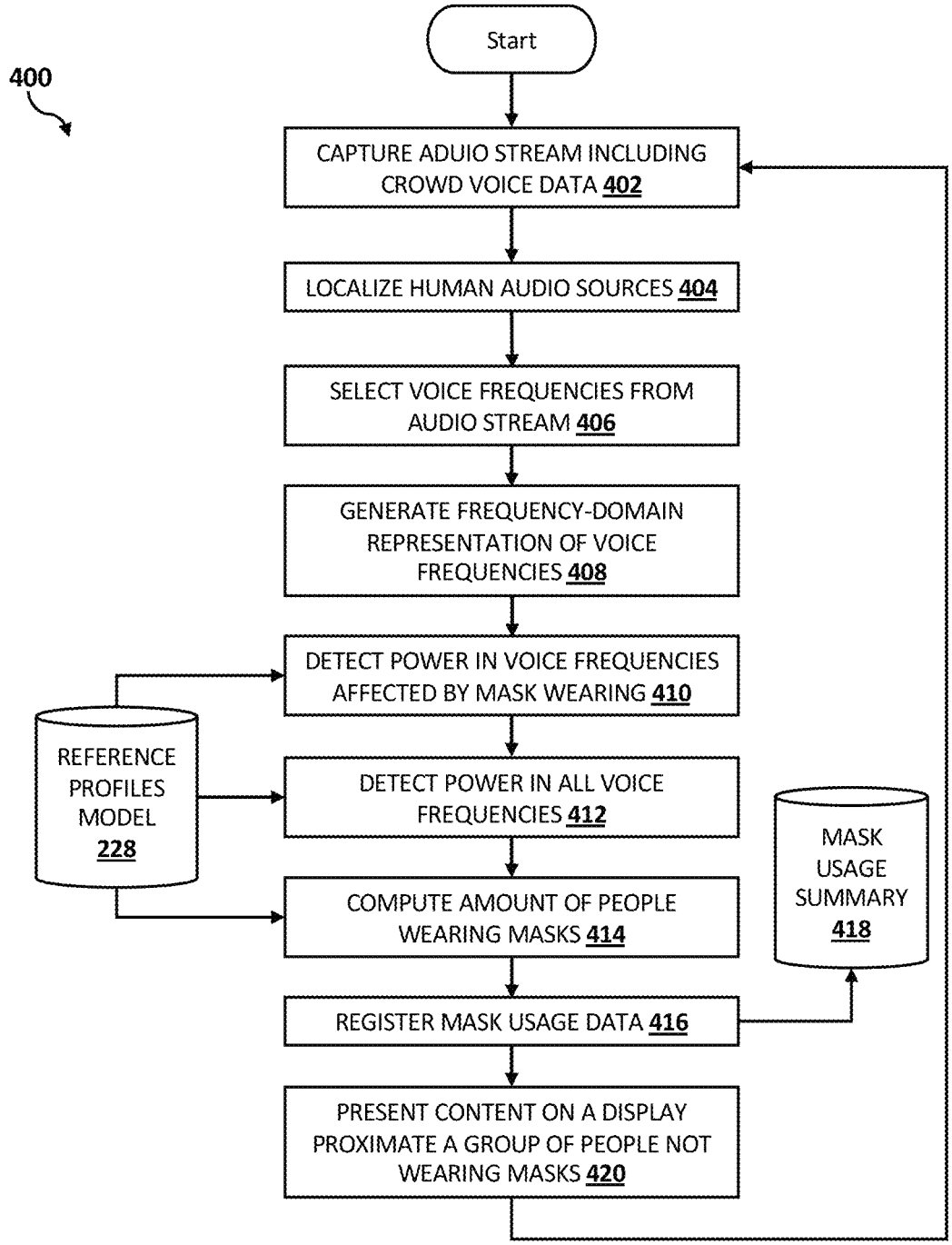
FIG. 4 is an operational flowchart illustrating a process for face mask detection based on crowd sounds according to at least one embodiment.

Referring now to FIG. 4, an operational flowchart illustrating an exemplary face mask detection process 400 based on crowd sounds used by the acoustic analysis program 110a, 110b according to at least one embodiment is depicted.

At 402, an audio stream including crowd voice data is captured. According to at least one embodiment of the present disclosure, one or more sensors, such as, for example, an array of microphones may detect and capture audio streams a venue. In various embodiments, the audio streams may include voice data from people may be speaking in proximity of the array of microphones. In at least one embodiment, the audio analysis program 110a, 110b may receive the captured audio streams from the array of microphones as an aggregate audio signal, as described previously with reference to FIG. 2.

Then, at 404, one or more human audio sources are localized. According to one embodiment, the audio analysis program 110a, 110b may implement the audio streams captured by the array of microphones to perform acoustic source localization, as described previously with reference to FIG. 2. According to one embodiment, the audio analysis program 110a, 110b may associate a microphone (e.g., of the array of microphones) with a zone or region of the venue that is closest to the microphone. As such, in response to determining that a sound was received by a microphone (e.g., by measuring distance and/or direction using triangulation and/or time difference of arrival (TDOA) techniques), the audio analysis program 110a, 110b may determine that the source of the sound (e.g., one or more speakers) may currently be found in the region of the venue that is closest to that microphone. According to one embodiment, in addition to determining the location (e.g., region) of the speakers in the venue, the audio analysis program 110a, 110b may use the acoustic source localization process to determine a total number of people within the venue.

Then at 406, voice frequencies are selected from the audio stream. In one embodiment, the audio streams captured by the array of microphones may include background noise (e.g., traffic noise, dogs barking, music) based on the environment of the venue. In various embodiments, audio analysis program 110a, 110b may filter out these background noises using suitable acoustic filtering techniques such that only the human voice sounds are included in the captured audio streams.

Then at 408, a frequency-domain representation of the voice frequencies are generated. According to one embodiment, the captured audio streams and the aggregated audio signal may initially include a time-domain representation. As such, the acoustic analysis program 110a, 110b may convert the time-domain representation of the aggregated audio signal using FFT into the frequency-domain representation as described previously with reference to FIG. 2. In one embodiment, the output of the FFT of the aggregated audio signal may include a cosine graph with power or magnitude value (e.g., amplitude or signal strength) for each frequency band in the frequency-domain representation of the aggregated audio signal. In one embodiment, it is contemplated that the frequency-domain representation of human voice frequencies (e.g., as included in the aggregated audio signal) may include a frequency range between 80-4000 Hz (although this is not limiting). As such, in one exemplary embodiment, the frequency-domain representation may include a power value for each of those frequency bands.

Then at 410, the power in voice frequencies affected by mask wearing is detected. As described previously with reference to FIG. 2, when a person is wearing a face mask, the audio analysis program 110a, 110b may detect a greater degree of sound attenuation and transmission loss in higher bands of the frequency spectrum. It is contemplated that sound attenuation, also referred to as frequency attenuation, may be detected based on a decrease in the power (e.g., amplitude or signal strength) in a given frequency band. Thus, in at least one embodiment, frequency attenuation resulting from wearing face mask may be detected based on the decrease in power in the higher frequency bands of the frequency spectrum (e.g., above frequencies of 3000 Hz). In one embodiment, the power in the high frequency bands may be measured as the average power available over the given frequency band (e.g., between 3000-4000 Hz). In one embodiment, the power values may be determined from the frequency-domain representation generated at process 408.

Then at 412, the power in all voice frequencies are detected. According to one embodiment, it is contemplated that the frequency-domain representation of human voice frequencies may include a frequency range between 80-4000 Hz. As such, in one exemplary embodiment, the frequency-domain representation may include a power value (e.g., may be zero) for each of those frequency bands. In one embodiment, the acoustic analysis program 110a, 110b may calculate the power across all the frequency bands as the total average power of all the frequency components of the signal. In one embodiment, the power values may be determined from the frequency-domain representation generated at process 408.

Then at 414, an amount of people wearing masks is computed. According to one embodiment, the acoustic analysis program 110a, 110b may compare the power distribution of the current crowd sounds (e.g., captured in the aggregated audio signal) against the reference power distributions of one or more reference recordings to determine (e.g., estimate) the current crowd's degree of mask-wearing compliance. The reference recordings may be associated with a reference percentage of people wearing face masks.

According to one embodiment, the reference profiles model 228 trained using training process 300 (FIG. 3) may store reference recordings of crowd sounds with different (known) percentages of face mask-wearing compliance with corresponding power distributions. In at least one embodiment, the power distributions may be described as a ratio between the power in the high frequency bands (e.g., 3000 Hz and above) and the power across all the frequency bands (e.g., 80-4000 Hz) in the frequency spectrum. According to one embodiment, the acoustic analysis program 110a, 110b may compute a current power distribution (e.g., ratio of power in frequency bands affected by mask wearing (process 410) to power in all voice frequency bands (process 412)) associated with the current crowd sounds. Then, the acoustic analysis program 110a, 110b may compare that current power distribution to each of the power distributions associated with the various reference recordings stored in the reference profiles model 228. In one embodiment, once the acoustic analysis program 110a, 110b matches the current power distribution to one of the power distributions in the reference profiles model 228, the acoustic analysis program 110a, 110b may determine that percentage of the reference recording as the current crowd's degree of mask-wearing compliance.

Then at 416, mask usage data is registered. In one embodiment, the acoustic analysis program 110a, 110b may store one or more mask usage data (e.g., amount of people wearing masks) in a mask usage summary database 418. In one embodiment, the mask usage data may be stored as a percentage of people wearing face masks and/or not wearing face masks. In one embodiment, the mask usage summary database 418 may be accessed by venue stakeholders to determine the amount of compliance within that venue.

Thereafter at 420, content is presented on a display that is proximate to a group of people not wearing face masks. According to one embodiment, the audio analysis program 110a, 110b may associate one or more displays with the regions of the venue that are closest to the displays. As such, in response to the audio analysis program 110a, 110b detecting one or more non-compliance regions of the venue where one or more speakers may not be wearing face masks, the audio analysis program 110a, 110b may present content to promote mask wearing on the display that is proximate to the non-compliance region. In one embodiment, if the current crowd's degree of mask-wearing compliance does not meet a configurable compliance threshold (e.g., 75% of people wearing face masks), the audio analysis program 110a, 110b may determine the location of the people that are not wearing face masks (e.g., detect the non-compliance region in the venue) and transmit one or more content to promote mask-wearing on the one or more displays that are proximate to the non-compliance region. According to one embodiment, the face mask detection process 400 may then return to 402 to provide continuous real-time face mask detection within a venue.

Accordingly, the audio analysis program 110a, 110b may improve the functionality of a computer because the audio analysis program 110a, 110b may enable the computer to interact with a microphone array to detect acoustic features in a privacy-preserving manner. In one embodiment, the audio analysis program 110a, 110b may enable the computer to use a microphone array to register the region around the microphone array where people may not using any face covering as detected by acoustics. In one embodiment, the audio analysis program 110a, 110b may enable the computer to use acoustic features to identify the amount of people around the microphone array and the amount of those people using face masks. In one embodiment, the audio analysis program 110a, 110b may enable the computer to use acoustic filters to reduce noise and amplify human voice frequencies. In one embodiment, the audio analysis program 110a, 110b may enable the computer to use one or more display capabilities connected to the microphone array to promote compliance with public health protocols. It is contemplated that the audio analysis program 110a, 110b may include additional use cases in various embodiments, such as, for example, to detect employee protective equipment usage, preventive maintenance, and health monitoring.

It may be appreciated that FIGS. 2 to 4 provide only an illustration of one embodiment and do not imply any limitations with regard to how different embodiments may be implemented. Many modifications to the depicted embodiment(s) may be made based on design and implementation requirements.

Figure 5:
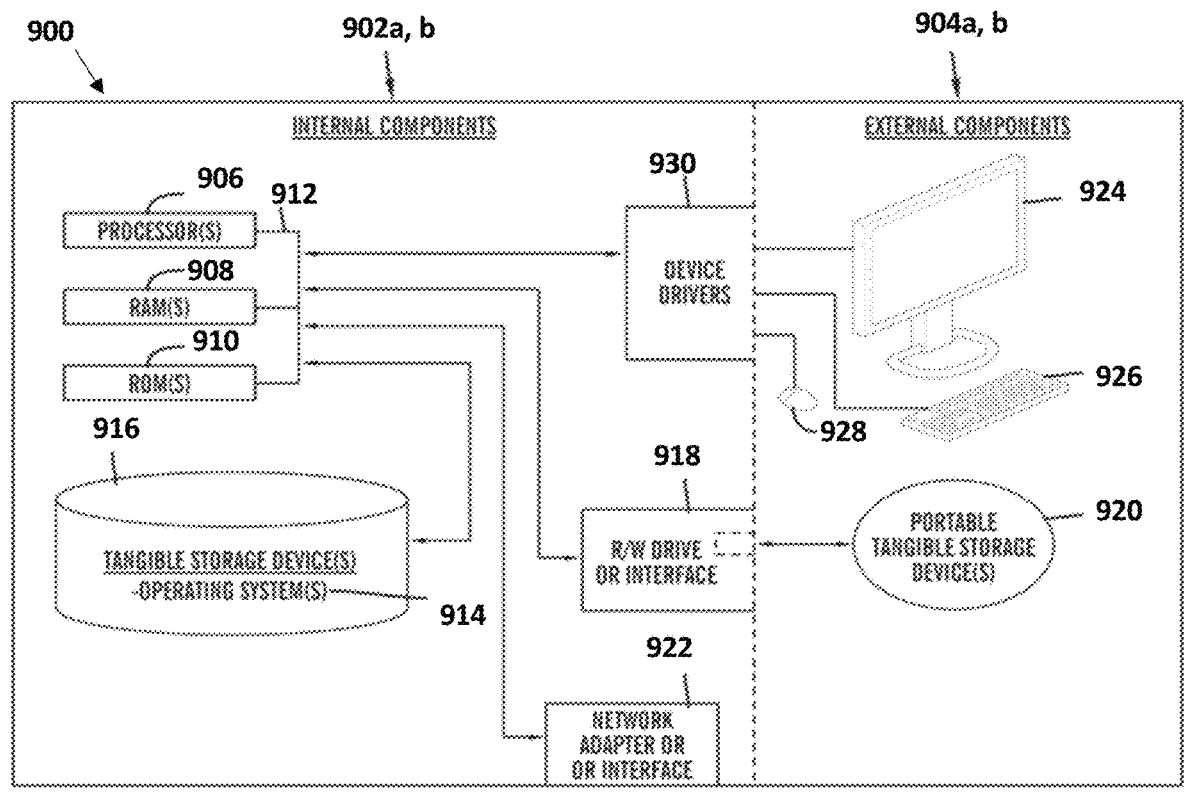
FIG. 5 is a block diagram of internal and external components of computers and servers depicted in FIG. 1 according to at least one embodiment.

FIG. 5 is a block diagram 900 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 5. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the audio analysis program 110a in client computer 102, and the audio analysis program 110b in network server 112, may be stored on one or more computer-readable tangible storage devices 916 for execution by one or more processors 906 via one or more RAMs 908 (which typically include cache memory). In the embodiment illustrated in FIG. 5, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the audio analysis program 110a and 110b can be stored on one or more of the respective portable computer-readable tangible storage devices 920, read via the respective RAY drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the audio analysis program 110a in client computer 102 and the audio analysis program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the audio analysis program 110a in client computer 102 and the audio analysis program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
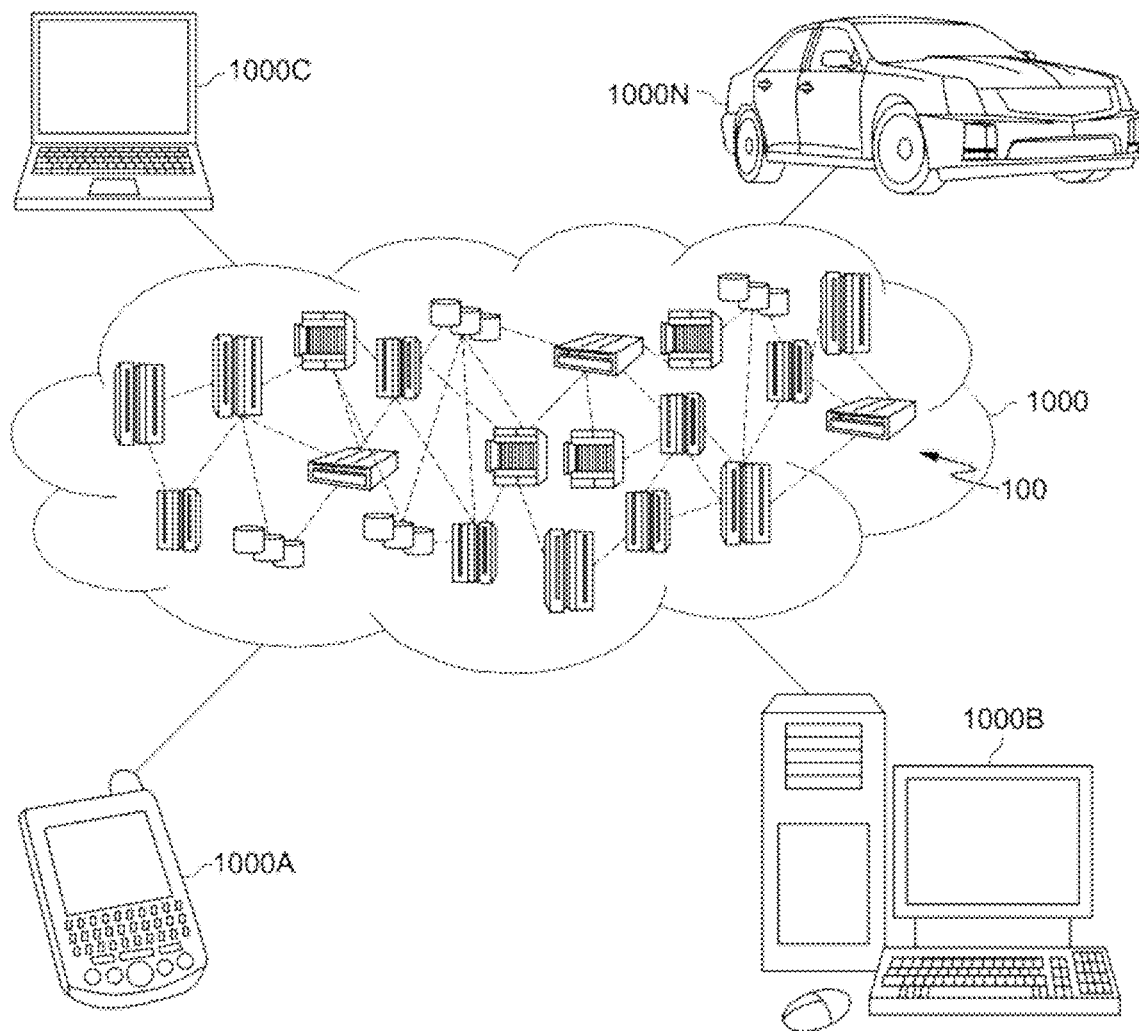
FIG. 6 is a block diagram of an illustrative cloud computing environment including the computer system depicted in FIG. 1, in accordance with an embodiment of the present disclosure.

Referring now to FIG. 6, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 6 are intended to be illustrative only and that computing nodes 100 and cloud computing environment 1000 can communicate with any type of computerized device over any type of network and/or network addressable connection (e.g., using a web browser).

Figure 7:
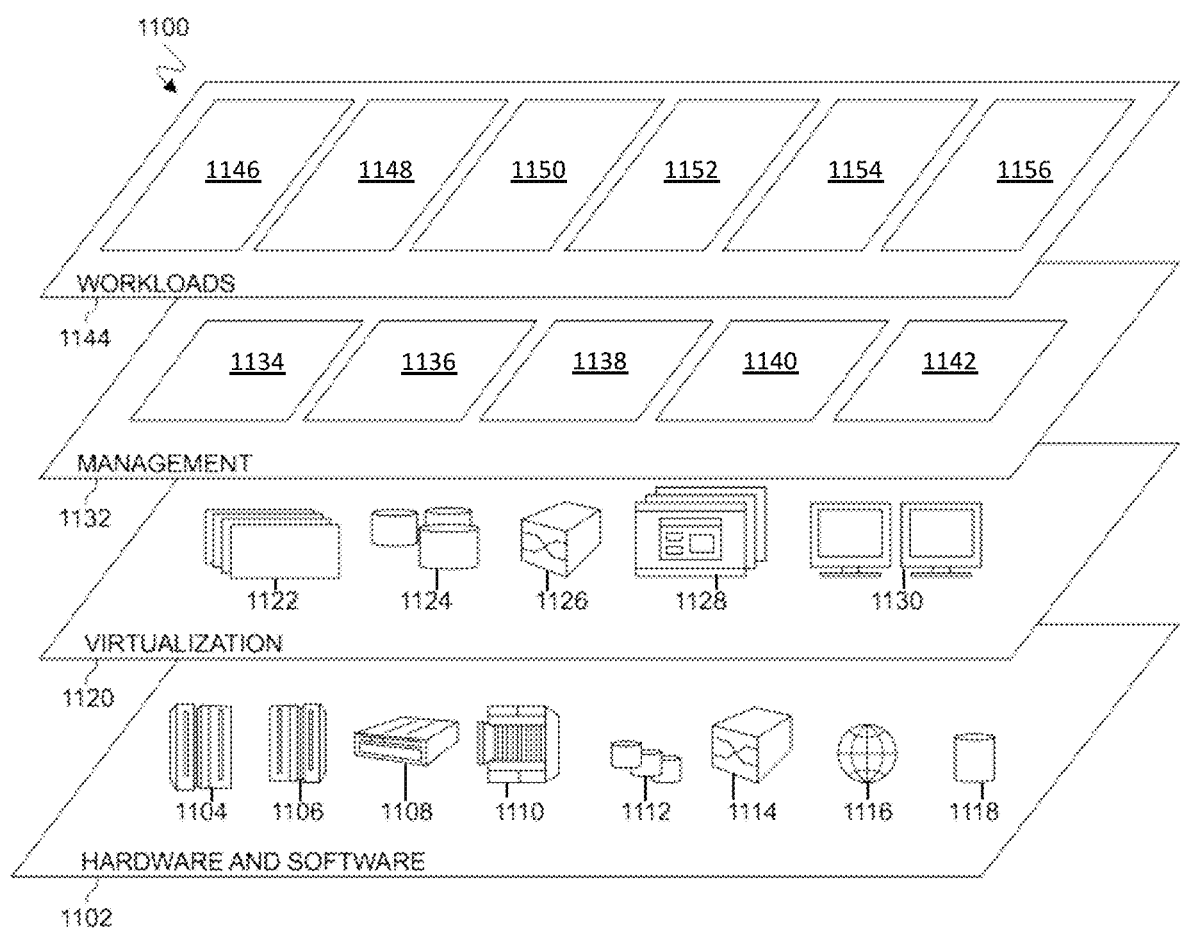
FIG. 7 is a block diagram of functional layers of the illustrative cloud computing environment of FIG. 6, in accordance with an embodiment of the present disclosure.

Referring now to FIG. 7, a set of functional abstraction layers 1100 provided by cloud computing environment 1000 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124;

virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and audio analysis 1156. A audio analysis program 110a, 110b provides a way to detect face mask usage based on acoustic analysis of crowd sounds.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
capturing an audio stream in a venue including a group of people, wherein the audio stream includes a crowd voice data;
analyzing the crowd voice data using a machine learning model to determine an amount of people wearing face masks in the venue; and
in response to determining that the amount of people wearing face masks does not meet a compliance threshold, displaying a content to the group of people in the venue to promote face mask usage.

2. The method of claim 1, wherein the machine learning model is trained to detect at least one acoustic feature associated with the amount of people wearing masks.

3. The method of claim 1, wherein capturing the audio stream including the crowd voice data further comprises:
capturing, using an array of microphones provided in the venue, a crowd sound of ambient speech produced by a plurality of people in proximity of the array of microphones.

4. The method of claim 1, further comprising:
receiving the captured audio stream as an aggregated audio signal, wherein the aggregated audio signal includes a plurality of voice frequencies produced by the group of people in the venue; and
generating a frequency-domain representation of the aggregated audio signal.

5. The method of claim 3, further comprising:
configuring the venue into a plurality of regions;
associating a first microphone of the array of microphones with a corresponding region of the plurality of regions that is closest to the microphone; and
in response to determining that the crowd sound was captured by the first microphone, locating a source of the crowd sound in the corresponding region of the plurality of regions of the venue.

6. The method of claim 3, further comprising:
detecting at least one non-compliance region in the venue, wherein the detected at least one non-compliance region in the venue is associated with a location including the plurality of people that are not wearing face masks;
identifying at least one display in the venue that is proximate to the non-compliance region; and
presenting at least one content on the identified at least one display to promote face mask-wearing compliance.

7. The method of claim 4, further comprising:
determining a power distribution based on the generated frequency-domain representation of the aggregated audio signal;
identifying at least one reference power distribution that matches the determined power distribution, wherein the identified at least one reference power distribution is associated with a reference percentage of people wearing face masks; and
computing the amount of people wearing face masks in the venue based on the reference percentage of people associated with the identified at least one reference power distribution matching the determined power distribution.

8. A computer system for detecting face mask usage based on a crowd sound, comprising:
one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is capable of performing a method comprising:
capturing an audio stream in a venue including a group of people, wherein the audio stream includes a crowd voice data;
analyzing the crowd voice data using a machine learning model to determine an amount of people wearing face masks in the venue; and
in response to determining that the amount of people wearing face masks does not meet a compliance threshold, displaying a content to the group of people in the venue to promote face mask usage.

9. The computer system of claim 8, wherein the machine learning model is trained to detect at least one acoustic feature associated with the amount of people wearing masks.

10. The computer system of claim 8, wherein capturing the audio stream including the crowd voice data further comprises:

capturing, using an array of microphones provided in the venue, a crowd sound of ambient speech produced by a plurality of people in proximity of the array of microphones.

11. The computer system of claim 8, further comprising:
receiving the captured audio stream as an aggregated audio signal, wherein the aggregated audio signal includes a plurality of voice frequencies produced by the group of people in the venue; and
generating a frequency-domain representation of the aggregated audio signal.

12. The computer system of claim 10, further comprising:
configuring the venue into a plurality of regions;
associating a first microphone of the array of microphones with a corresponding region of the plurality of regions that is closest to the microphone; and
in response to determining that the crowd sound was captured by the first microphone, locating a source of the crowd sound in the corresponding region of the plurality of regions of the venue.

13. The computer system of claim 10, further comprising:
detecting at least one non-compliance region in the venue, wherein the detected at least one non-compliance region in the venue is associated with a location including the plurality of people that are not wearing face masks;
identifying at least one display in the venue that is proximate to the non-compliance region; and
presenting at least one content on the identified at least one display to promote face mask-wearing compliance.

14. The computer system of claim 11, further comprising:
determining a power distribution based on the generated frequency-domain representation of the aggregated audio signal;
identifying at least one reference power distribution that matches the determined power distribution, wherein the identified at least one reference power distribution is associated with a reference percentage of people wearing face masks; and
computing the amount of people wearing face masks in the venue based on the reference percentage of people associated with the identified at least one reference power distribution matching the determined power distribution.

15. A computer program product for detecting face mask usage based on a crowd sound, comprising:
one or more computer-readable storage media and program instructions collectively stored on the one or more computer-readable storage media, the program instructions executable by a processor to cause the processor to perform a method comprising:
capturing an audio stream in a venue including a group of people, wherein the audio stream includes a crowd voice data;
analyzing the crowd voice data using a machine learning model to determine an amount of people wearing face masks in the venue; and
in response to determining that the amount of people wearing face masks does not meet a compliance threshold, displaying a content to the group of people in the venue to promote face mask usage.

16. The computer program product of claim 15, wherein the machine learning model is trained to detect at least one acoustic feature associated with the amount of people wearing masks.

17. The computer program product of claim 15, wherein capturing the audio stream including the crowd voice data further comprises:
capturing, using an array of microphones provided in the venue, a crowd sound of ambient speech produced by a plurality of people in proximity of the array of microphones.

18. The computer program product of claim 15, further comprising:
receiving the captured audio stream as an aggregated audio signal, wherein the aggregated audio signal includes a plurality of voice frequencies produced by the group of people in the venue; and
generating a frequency-domain representation of the aggregated audio signal.

19. The computer program product of claim 17, further comprising:
configuring the venue into a plurality of regions;
associating a first microphone of the array of microphones with a corresponding region of the plurality of regions that is closest to the microphone; and
in response to determining that the crowd sound was captured by the first microphone, locating a source of the crowd sound in the corresponding region of the plurality of regions of the venue.

20. The computer program product of claim 17, further comprising:
detecting at least one non-compliance region in the venue, wherein the detected at least one non-compliance region in the venue is associated with a location including the plurality of people that are not wearing face masks;
identifying at least one display in the venue that is proximate to the non-compliance region; and
presenting at least one content on the identified at least one display to promote face mask-wearing compliance.

* * * * *